US005571206A

United States Patent [19]
Varn

[11] Patent Number: 5,571,206
[45] Date of Patent: Nov. 5, 1996

[54] LEG AMPUTEE ORTHOSIS

[75] Inventor: Harold T. Varn, Lawrenceville, Ga.

[73] Assignee: Restorative Care Of America Incorporated, Clearwater, Fla.

[21] Appl. No.: 243,117

[22] Filed: May 16, 1994

[51] Int. Cl.⁶ .................................................... A61F 2/50
[52] U.S. Cl. ................................ 623/27; 623/35; 602/23; 602/26
[58] Field of Search ..................... 602/5, 16, 209, 602/23, 26; 623/27, 32, 35, 36, 39

[56] References Cited

U.S. PATENT DOCUMENTS

| | | | |
|---|---|---|---|
| 288,239 | 11/1883 | Ingram | 623/27 X |
| 710,996 | 10/1902 | Peer | 623/36 X |
| 804,207 | 1/1905 | Bunderle | 623/35 |
| 1,032,074 | 7/1912 | Marks | 623/32 X |
| 1,340,236 | 5/1920 | Nelson | 623/32 |
| 1,419,791 | 6/1922 | Wehrman | 623/27 X |
| 1,861,311 | 5/1932 | Logan | 623/27 X |
| 2,545,843 | 8/1949 | Cohan . | |
| 2,570,581 | 10/1951 | McIntyre | 623/32 |
| 2,632,440 | 3/1953 | Hauser et al. | 602/16 |
| 4,489,717 | 12/1984 | Moissonnier | 602/16 |
| 4,489,718 | 12/1984 | Martin | 602/16 |
| 4,612,919 | 9/1986 | Best | 602/16 |
| 4,632,096 | 12/1986 | Harris | 602/16 |
| 4,681,097 | 7/1987 | Pansiera . | |
| 4,697,808 | 10/1987 | Larson et al. | 623/27 X |
| 4,776,326 | 10/1988 | Young et al. | 602/26 X |
| 4,817,588 | 4/1989 | Bledsoe | 602/16 |
| 4,848,326 | 7/1989 | Lonardo . | |
| 4,947,835 | 8/1990 | Hepburn et al. | 602/16 |
| 5,018,514 | 5/1991 | Grood et al. | 602/26 X |
| 5,108,455 | 4/1992 | Telikicherla | 623/36 X |
| 5,306,230 | 4/1994 | Bodine | 602/26 |
| 5,328,446 | 7/1994 | Bunnell et al. | 602/26 X |
| 5,358,469 | 10/1994 | Patchel et al. | 602/26 X |

Primary Examiner—Richard J. Apley
Assistant Examiner—David R. Risley
Attorney, Agent, or Firm—Zarley, McKee, Thomte, Voorhees & Sease

[57] ABSTRACT

An orthosis and method for treating knee contractures in leg amputees includes a pair of upper splints with a thigh band extending therebetween, and a pair of lower splints with a calf band extending therebetween with opposite sides and a space therebetween for receiving a residual limb. Dial-lock hinges pivotally and lockably connect the upper and lower splints so that the relative angular position of the splints can be varied. Straps and padding are provided on the bands to comfortably restrain the leg. A removable calf liner pads the residual limb and has extra padding below the patient's patella for cushioning the tendons from pressure. An optional removable cover mounts over the space on the calf band, providing diametrical adjustability and access to the residual limb. The method for treating leg amputee knee contractures includes providing the orthosis, positioning the leg in the orthosis, restraining the leg therein, selecting an angle between the splints and locking the hinges so as to apply passive tension, maintaining such tension for a prescribed period, and repeating the selecting, locking, and maintaining steps to increase the tension in increments until the contracture is corrected.

20 Claims, 3 Drawing Sheets

LEG AMPUTEE ORTHOSIS

BACKGROUND OF THE INVENTION

The invention described herein relates to the field of therapeutic devices attachable to the joints of the human body, in particular corrective devices for attachment to the leg of below-the-knee leg amputees for correcting flexion contractures of the knee joint.

As a consequence of their illnesses and injuries or indirectly from curling up in reaction to the phenomena of phantom pain, many below-the-knee amputees suffer from flexion contracture of the knee joint. In this condition, the knee joint stays flexed or bent, resists movement, and the patient does not enjoy the normal full range of mobility. For amputees this is a particularly troublesome problem because the contracture impedes the process of fitting them with a suitable prosthetic device. The length of the prosthesis and its load bearing structure are affected by the position of the knee and residual limb. If an improvement in a knee contracture condition takes place subsequent to fitting the patient with a prosthesis, a retrofit or replacement may be required. Since prosthesis are generally custom designed and built, this can be quite costly. Therefore, it is customary to treat any knee flexion contracture soon after the amputation and before the prosthetic device is designed and built.

However, existing means and methods for treating knee flexion contractures have not proven to be well adapted to the needs of amputees or their care providers. One common means of treating knee contractures is with bandages and plaster of paris casts. A series of plaster casts are applied between conventional physical therapy sessions. The process is time-consuming, messy, and expensive. Furthermore, while the physician is typically concerned about the possibility of infection at or near the site of the amputation, the area of concern is usually obscured from view by the plaster cast.

Some occupational therapists lay the leg in a trough or gutter to passively accommodate the joint in hopes that mere gravity will eventually return full extension to the knee. Various elastic bandages and knee braces or immobilizers are known to be applicable to knee contractures, but these devices are not well suited for use by leg amputees. The residual limb of an amputee normally extends only about six to nine inches below knee center and such devices typically cover the amputation site, obscuring possible infections and the like from the view of the care provider. Many of the conventional devices also apply unwanted pressure on the residual limb. The residual limb is usually quite sensitive to any contact for some time after the amputation surgery. Finally, many of the existing devices must be custom fit and are therefore quite expensive.

Therefore, it is a primary object of this invention to provide a leg amputee knee corrective orthosis which can be applied at the conclusion of the amputation surgery to passively stretch the joint and yet allow the physician easy access to examine the residual limb without destroying the orthosis.

A further object of this invention is to provide an orthosis which provides an easily adjustable amount of passive corrective tension to the knee joint.

A further object of this invention is to provide a leg amputee knee corrective orthosis which is quickly and easily adjustable to fit various patients, yet capable of being mass produced rather than custom made.

A further object of this invention is to provide a single leg orthosis which can be used on either the right or left leg of the patient.

A further object of this invention is to provide an orthosis which is quickly and easily attached to the leg of an amputee without the use of messy plasters and the like.

A further object of this invention is to provide an orthosis which is durable in use and economical to manufacture.

A further object of this invention is to provide an orthosis which accommodates, controls, and helps ease post-surgery swelling or edema.

A further object of this invention is to provide an orthosis through which drainage tubes can be attached to the residual limb, if needed.

A further object of this invention is to provide an orthosis with a lower end which can accommodate a prosthesis or artificial limb.

A further object of this invention is to provide an orthosis which has padding under the patella to absorb some of the forces which the underlying tendons are subjected to by the patient's prosthesis during ambulation.

A further object of this invention is to provide an orthosis having a soft, absorbent liner and cuff which render the orthosis comfortable to wear.

These and other objects will be apparent to one skilled in the art from the description which follows.

SUMMARY OF THE INVENTION

The present invention is an orthosis and method for correcting knee flexion contractures which are often suffered by below-the-knee leg amputees. Whether immediately after amputation surgery or in subsequent treatment, the orthosis can be applied to the patient's knee joint, placing the joint under gradually progressive increments of passive tension until the desired extension and range of movement is obtained. The orthosis can be applied, without modification, to either the left or right leg.

The orthosis includes thigh and calf portions having substantially parallel lateral splints. The splints are pivotally connected along the sides of the knee by dial-lock hinges. The upper portion of the thigh splints are attached to a transverse cross member or thigh band. The calf portion splints are attached to the sides of a calf-receiving band. The calf band can include a removable sleeve or cover to give greater access for medical personnel to monitor the residual limb. Straps are operatively attached to the curved calf band, cover, and thigh band to secure the orthosis to the patient's upper leg and residual limb. Appropriate soft, absorbent, and washable padding, in the form of a cuff and a calf liner, is provided for the comfort of the patient and ease of use. Hook and loop fasteners on the straps and liner make the device easy to apply and remove.

The dial-lock hinges of the orthosis allow the thigh and calf splints on either side of the knee joint to be selectively pivoted about a screw which brings inwardly directed teeth on the thigh splints into engagement with mating outwardly directed teeth on the calf splints. When the screws are sufficiently loosened, the teeth disengage and the relative angular position of the leg and calf portions is adjustable.

The orthosis and method of this invention are particularly adapted to serve the needs of below-the-knee leg amputees and their care providers. For example, the calf liner includes extra padding where it covers the tendons below the patella. Thus, the tendons are well cushioned when beared upon or rubbed by the calf portion, especially when the patient ambulates with an artificial limb or reclines.

The method of this invention includes providing the orthosis, positioning the leg in the orthosis, restraining the leg, and using the dial-lock hinges to apply passive tension in increasing increments over time to correct the contractive.

DETAILED DESCRIPTION OF THE PREFERRED EMBODIMENT

Figure 1:
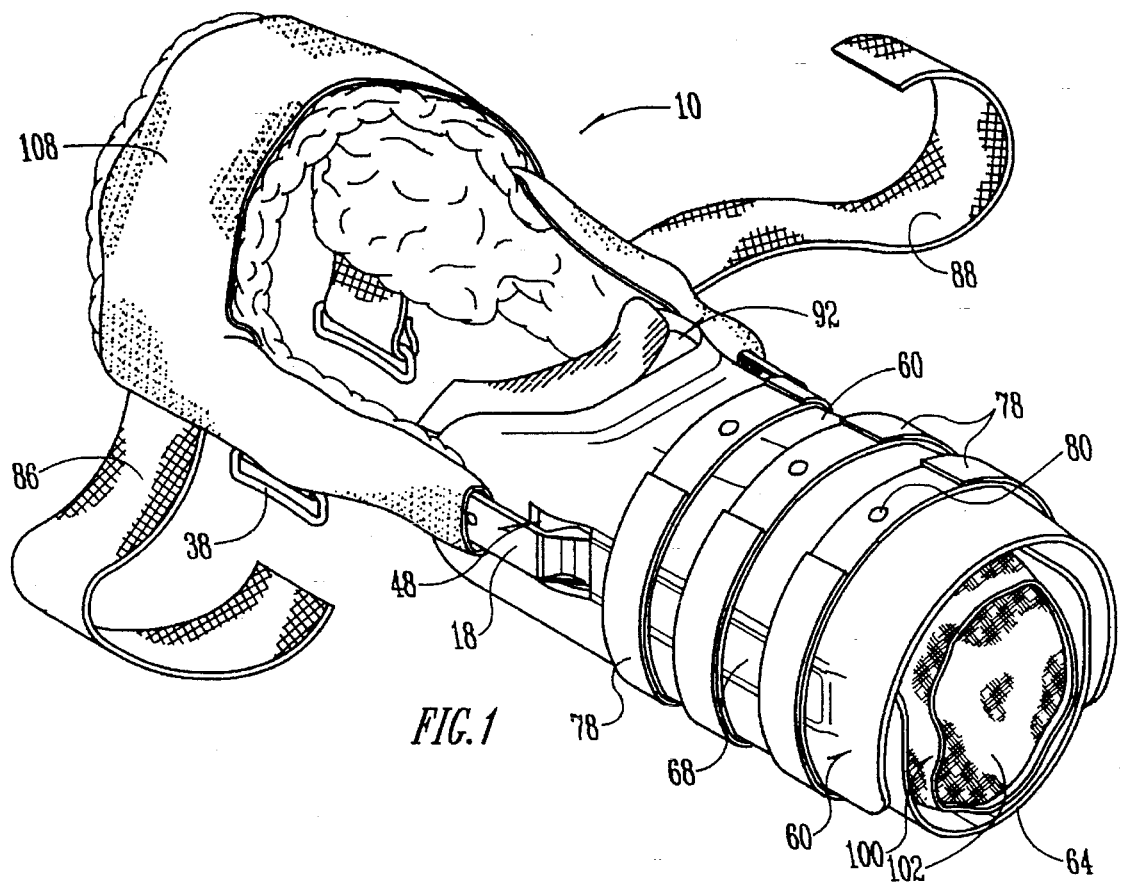
FIG. 1 is a perspective view of the posterior of the leg corrective orthosis of this invention.
Figure 2:
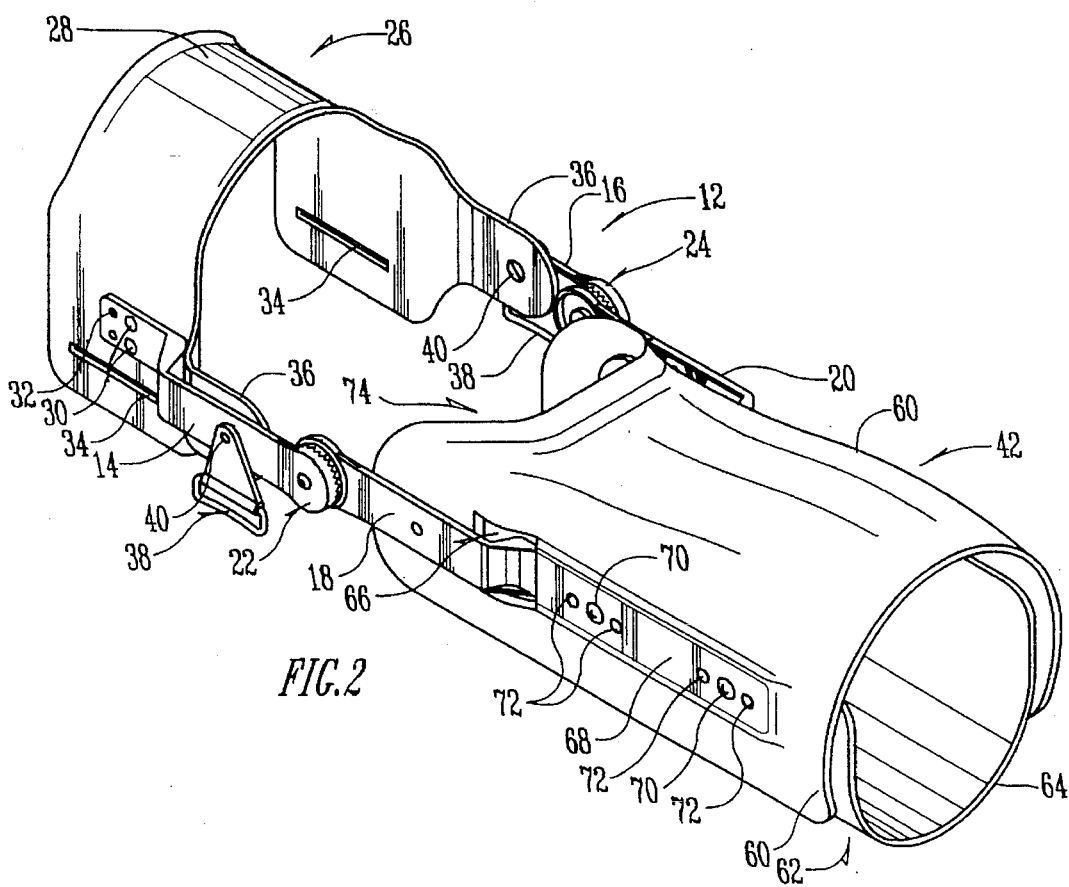
FIG. 2 is a perspective view of the posterior of the two-part hinged frame of the orthosis.
Figure 7:
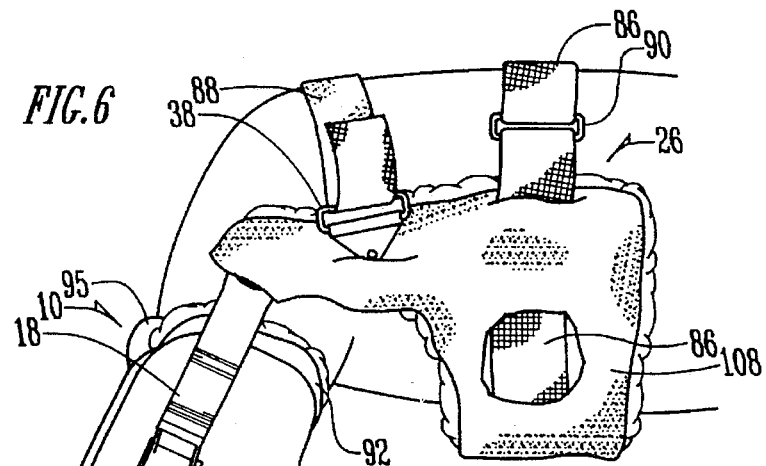
FIG. 7 is a perspective view of the orthosis as applied to the knee joint of a leg amputee.

The leg amputee corrective orthosis of this invention is generally shown in FIG. 1 and referenced by the numeral 10. As shown in FIG. 7, the orthosis 10 is useful in correcting joint flexion contractures of the knee on patients having an amputated leg. In FIG. 2, orthosis 10 is shown to have a rigid, but pivotable underlying frame 12. The frame 12 includes a pair of substantially parallel upper splints 14,16 which are pivotally joined to a pair of lower splints 18,20 by dial-lock hinges 22,24.

The thigh portion 26 of frame 12 is adapted to receive the thigh of the amputee and includes the pair of fixed length upper splints 14,16 extending laterally along the thigh and a curved cross member or thigh band 28 which interconnects the upper ends of splints 14,16. Conventional fastening means, such as rivets 30, secure the sides of thigh band 28 to the upper ends of splints 14,16 through a plurality of mounting holes 32. Mounting holes 32 are spaced apart along the length of splints 14,16 so as to provide means for adjusting the longitudinal span of thigh portion 26 to accommodate the size of the patient's leg. It is also contemplated that using detachable fastening means, such as nuts and bolts, screws, or the like rather than rivets would provide additional adjustability even after the orthosis is initially assembled.

Longitudinal slots 34 extend through each side of thigh band 28. Both sides of the lower portion of thigh band 28 have outwardly formed and downwardly extending ears 36 to which upper splints 14,16 are secured along with buckle 38 pivotably mounted thereon by conventional means, such as rivets 40. For comfort and handling ease, both the upper and lower perimeters of the posterior of thigh band flare outwardly.

Figure 4:
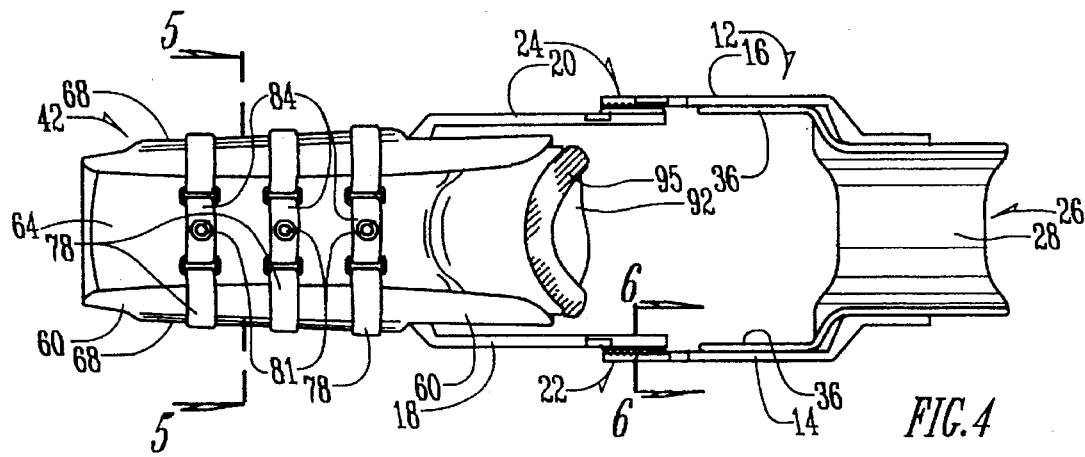
FIG. 4 is a view of the posterior of the frame of the orthosis showing the calf straps and dial-lock hinges.
Figure 6:
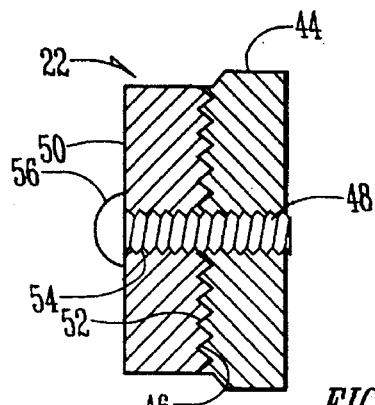
FIG. 6 is an enlarged sectional view taken along line 6—6 in FIG. 4 of the dial-lock hinges of the orthosis.

In FIGS. 2 and 4, upper and lower splints 14,16,18,20 are shown to be pivotally joined by bilateral dial-lock hinges 22,24 located about 180 degrees apart on the sides of thigh portion 26 and calf portion 42. As shown in FIG. 6, each dial-lock hinge 22,24 includes a disk 44 formed in the upper end of lower splints 18,20. The outwardly facing side of disk 44 has a plurality of outwardly projecting teeth 46 spaced in a generally circular pattern around a threaded hole 48 in the center of disk 44. Another disk 50 is formed in the lower end of each upper splint 14,16. The inwardly facing side of disk 50 has a plurality of inwardly projecting teeth 52 spaced in a generally circular pattern about a center hole 54. A screw 56 extends through the aligned holes 48,54.

The head of screw 56 can be constructed with a slot, socket, phillips, cap or other conventional configuration as necessary to accept the appropriate complementary tool. Screw 56 may even have an enlarged and knurled head to facilitate hand tightening. When screw 56 is tightened, as shown in FIG. 6, teeth 46 and 52 are matingly engaged and cannot rotate with respect to each other. When screw 56 is loosened sufficiently, teeth 46 and 52 are disengaged and can clear each other. In that condition, the angle between upper and lower splints 14,16,18,20 can be adjusted by rotating the splints relative to each other about the axis of screw 56. Such lockable adjustment makes orthosis 10 well-suited for correcting knee flexion contractures by gradually extending the joint with passive tension until full or maximum possible extension is achieved. After correction of the contracture, the leg amputee can be fitted with a permanent prosthesis.

As shown in FIG. 2, the calf portion 42 of frame 12 includes a curved calf band 60 with an anterior opening 62 for receiving the residual limb of an amputee. Preferably, a cover 64, which is roughly the same length as curved calf band 60, is fitted to the opening 62 so as to protect and hold the patient's residual limb. It is contemplated that the opening and cover could be positioned at the posterior of the leg instead of the anterior of the leg without detracting from the effectiveness of the invention. Preferably, thigh band 28, calf band 60 and cover 64 are constructed of a rigid, lightweight material, such as polyethylene plastic. Preferably, calf band 60 and cover 64 are made of translucent polyethylene plastic. Slots 66 are laterally disposed on either side of curved calf band 60. Lower splints 18,20 extend downwardly into each respective slot 66 and fit into a longitudinal sleeve 68 formed in the wall of calf band 60, as shown in FIG. 5.

Figure 3:
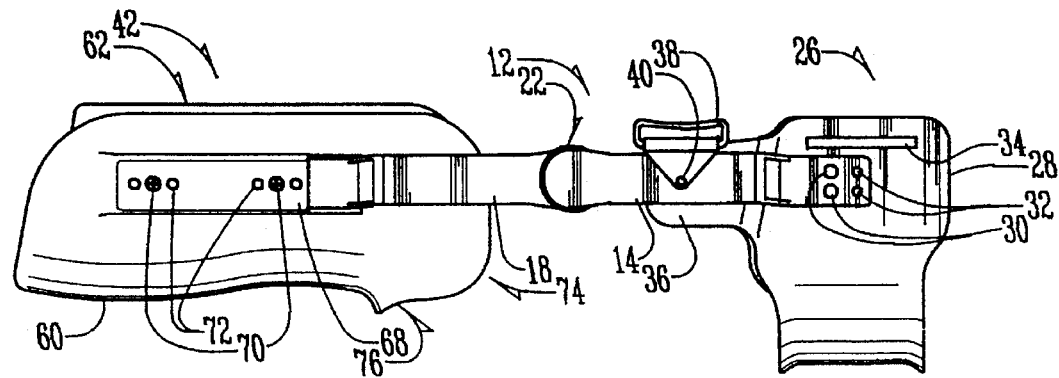
FIG. 3 is a side elevation view of the frame in position for full extension of the patient's knee.

As shown in FIGS. 2 and 3, lower splints 18,20 are fastened to calf band 60 by conventional means, such as screws 70 through one of a series of longitudinally spaced-apart mounting holes 72. Mounting holes 72 provide a means for longitudinal adjustment of the calf portion 42 of orthosis 10 to fit the patient's leg. For comfort and safety, screws 70 do not protrude through the lower splints 18,20. Lower splints 18,20 project outwardly at slots 66 then extend upwardly to either side of the knee joint where they form the bilateral dial-lock hinged connections 22,24 with upper splints 14,16.

Calf band 60 is shown to be open at both ends. An open lower end is advantageous for attaching a prosthesis or inserting drainage tubes into the residual limb to remove unwanted fluids. However, the lower end could also be closed if such drainage or prosthesis mounting is not required. The periphery of top 74 of curved calf band 60 is saddle-shaped, with a posterior recess 76 (see FIG. 3) for comfortably accommodating the leg of the patient whether the leg is flexed or extended. Preferably the lower end of calf band 60 extends below the end of the patient's residual limb so that an artificial limb or prosthesis (not shown) can be inserted into curved calf band 60 and fitted to the patient's residual limb. Of course, the prosthesis may also be adapted to fit to the outside of calf portion 42. Calf band 60 is preferably contoured to receive the residual limb and to outwardly resemble the human leg.

Figure 5:
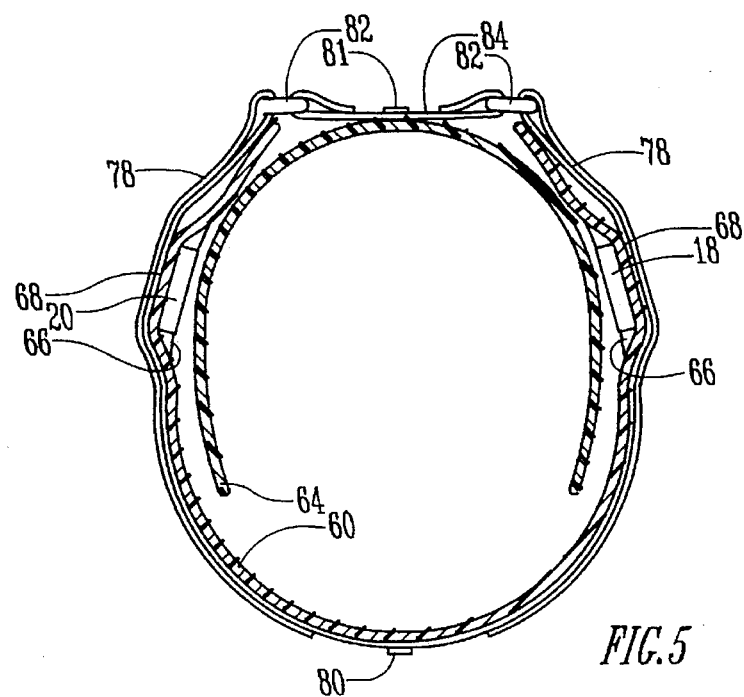
FIG. 5 is a sectional view taken along line 5—5 of FIG. 4 showing the cover fastened over the opening in the calf band of the orthosis.

In FIGS. 4 and 5, three straps 78 are shown to be fastened to cover 64 which is slidably inserted inside the anterior opening 62 in curved calf band 60 to form an expandable bivalve for enclosing the patient's residual limb. This expandable bivalve is advantageous because the residual limb is often subject to edema or swelling after the amputation surgery. With the orthosis assembled as shown in FIGS. 4 and 5, not only is the limb protected, but cover 64 shields the sides of the limb from contact with the lower splints 18,20.

Each transverse strap 78, which secures the cover 64, is spaced apart from the next and is fastened to calf band 60 by a rivet 80 (see FIG. 5) or other suitable, similarly nonobtrusive, conventional means of attachment. Straps 78 are made of hook and loop fastening material or have hook and loop material attached to them. Therefore, straps 78 are fastenable by doubling back on themselves after going through loops 82 which are disposed at either end of fabric buckles 84 fastened to cover 64 by conventional means, such as rivets 81. Straps 78 are also advantageously arranged so that they cover the heads of screws 70 (see FIGS. 1, 2, and 7) to prevent snagging of bed sheets, clothing, and the like.

In FIG. 7, orthosis 10 is secured to the upper part of the patient's leg by an upper strap 86 and a lower strap 88. Both straps 86 and 88 are equipped with hook and loop fasteners. Strap 86 encircles thigh band 28 and the patient's leg. Strap 86 passes through loop 90 and doubles back upon itself to be secured by hook and loop fasteners. Strap 88 passes through buckles 38 then its ends are doubled back on top of themselves to secure the anterior portion of the leg just above the knee. Strap 88 effectively prevents the residual limb from rising out of calf portion 42. With the orthosis 10 applied to the leg as described above, the angle between splints 14,16, 18,20 can be adjustably locked into a series of positions of further extension to improve the knee contracture condition.

Figure 8:
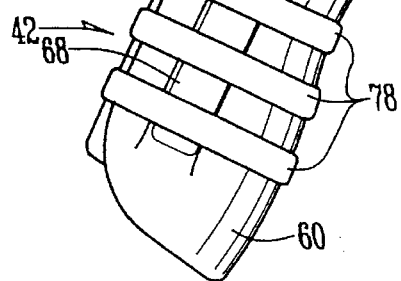
FIG. 8 is a perspective view of the laterally split padded calf liner of the orthosis.
Figure 8:
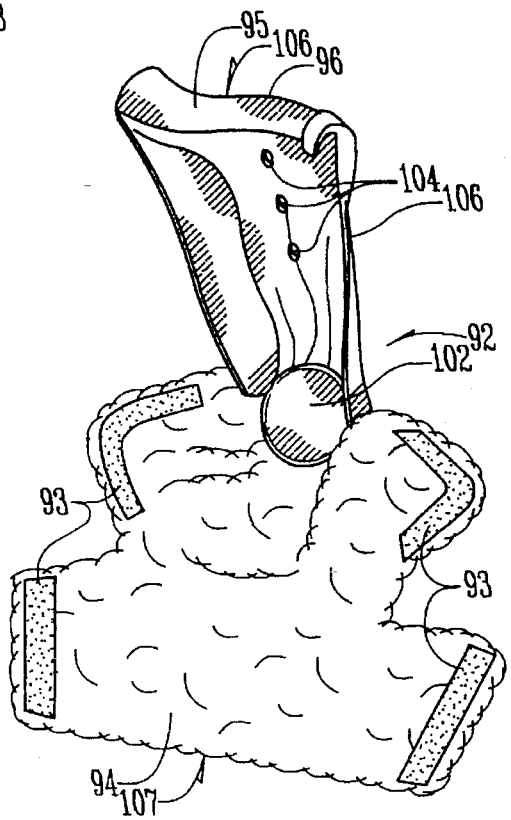

For the comfort of the wearer, a removable liner 92 is loosely inserted into calf portion 42. As shown in FIG. 8, liner 92 is preferably split laterally and is fastenable around the patient's residual limb by conventional hook and loop fasteners 93 located along the split lines. Referring to FIGS. 1 and 8, liner 92 has a padded inner side 94, an outer side 96 and a top opening 98 for receiving the calf of the patient's leg. Liner 92 also has a bottom opening 100 which is preferably covered with a soft cap 102 to protect the end of the patient's residual limb. Ventilation holes 104 are included in the anterior portion 106 of liner 92. In FIGS. 7 and 8, a patella pad 95 comprising an extra measure of padding is provided on the anterior portion of top opening 92. Patella pad 95 protects the patient's underlying tendons from undue pressure when the patient ambulates with a prosthesis. Patella pad 95 also protects from pressures caused when the patient reclines.

In FIG. 1, a padded thigh cuff 108 is detachably attached to thigh portion 26 using conventional hook and loop fasteners. Liner 92 and padded cuff 108 are constructed of a soft, absorbent material on the inside and a soft, durable material on the outside to which the hooks of conventional hook and loop fasteners will adhere. Because the cuff and liner are likely to become soiled with perspiration and other soilants, the respective materials are preferably machine or hand washable.

In use, the orthosis 10 may be applied at the end of the amputation surgery (contemporaneously) or a short time thereafter, or whenever the contracture condition presents itself. Preferably, the contracture correcting process is completed before the leg amputee is fitted for a permanent prosthesis. However, it is contemplated that the process can be continued after the prosthesis fitting. Thus, the inclusion of patella pad 95.

To fit the device 10 to the patient's leg, first the care provider prepares device 10 to receive the patient's leg. Straps 78, 86, and 88 are unfastened and cover 64 is removed. The anterior and posterior portions 106, 107 of laterally split liner 92 are separated and laid open in curved calf band 60 as shown in FIG. 8. The dial-lock hinges 22, 24 are either unlocked or set so that the angle between splints 14, 16 and 18, 20 approximates the current angle of the patient's leg at the knee joint.

Next, the care provider elevates or brings forward the leg and positions orthosis 10 underneath it. The upper leg and residual limb are then laid against the padded cuff 108 or thigh portion 26 and padded inner side 94 of calf liner 92, respectively. The anterior portion 106 of liner 92 is gently tucked around the residual limb of the patient and fastened to the posterior portion 107 by fasteners 93 (see FIG. 8).

Next, cover 64 is slid or otherwise maneuvered into place over the residual limb resting in calf band 60. (See FIG. 4) Straps 78 are threaded upwardly through the respective loops 82 on buckles 84, then are pulled downwardly along the outer sides of the curved calf band 60 until they snugly hold cover 64 against the opening 62. Then the straps are fastened in place by the hook and loop fasteners thereon.

Finally, with the leg restrained in orthosis 10, splints 14, 16, 18, 20 are adjusted to the desired angle for treatment and dial-lock hinges 22, 24 are locked. Because the angle for treatment is greater than the current angle of the patient's knee, the joint is placed in passive tension. As this tension is maintained over time, it gradually corrects the contracture condition. As the patient responds to therapy, the dial-lock hinges 22, 24 are used to gradually increase the angle between the patient's upper leg and residual limb in increments. Adjustment can be affected without completely removing the orthosis. The adjustment and locking steps are continued until full extension or maximum possible recovery is achieved.

The care provider can easily check the residual limb for edema, infection, or other concerns by loosening straps 78 and removing cover 64. Thus, the residual limb can be monitored without completely destroying, removing, or dismantling the orthosis. Treatment for the contracture is easily resumed with the same orthosis following such examination.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A leg orthosis for controlling knee flexion of a leg amputee having a residual limb extending below the knee, the orthosis comprising:

a pair of upper splints, each having upper and lower ends;

a pair of lower splints, each having upper and lower ends, the upper end of each lower splint being pivotally connected to the lower end of one of the upper splints at a pivot joint;

a curved thigh band extending between the upper splints to partially encircle the amputee's thigh;

a curved calf band connected to and extending between the lower splints for engaging the amputee's residual limb, and having opposite sides with a space therebetween for receiving the residual limb;

a curved cover having opposite sides and being removably mountable with the calf band for closing the space therein and thereby defining an adjustable bivalve for enclosing the residual limb;

calf straps attached to the calf band and extending over the cover for securing the calf band and cover around the residual limb, whereby the cover is mountable with the calf band after the residual limb is received in the calf band;

thigh straps for securing the thigh band to the amputee's thigh;

padding on the thigh band and calf band to engage the amputee's leg; and an adjustable lock on at least one of the pivot joints to allow the upper and lower splints to be releasably locked at selected angular orientations and thereby control flexion of the knee.

2. The orthosis of claim 1 wherein said calf straps each have a center portion and opposite ends, said center portion being connected to the curved calf band and said opposite ends being operatively fastened to the cover.

3. The orthosis of claim 1 wherein said calf band has a lower end which is open so as to allow access for drainage tubes to be attached to the residual limb.

4. The orthosis of claim 1 wherein said calf band has a lower end opposite the lock which is adapted to receive a prosthesis.

5. The orthosis of claim 3 wherein said liner includes a patella pad mounted on an upper end thereof proximate the lock and adjacent to the patella of the amputee for cushioning the tendons of the leg below the knee joint.

6. The orthosis of claim 1 wherein said padding on the calf band comprises a removable liner having a tubular shape to encircle the residual limb.

7. The orthosis of claim 6 wherein said liner has an open upper end and a capped lower end, said capped end being directed downwardly when the liner is inserted in the calf band.

8. The orthosis of claim 7 wherein said liner is split into a posterior section and an anterior section which are separable to allow the insertion of the patient's leg therebetween.

9. The orthosis of claim 1 wherein said thigh straps comprise an upper strap and a lower strap detachably mounted to the thigh band.

10. The orthosis of claim 1 wherein said space in the calf band is longitudinal and anterior.

11. The orthosis of claim 1 wherein said orthosis is substantially laterally symmetrical such that said orthosis may be used interchangeably on both right and left leg amputees.

12. The orthosis of claim 1 further comprising fasteners on the lower splints and the calf band for rigidly yet longitudinally adjustably attaching the lower splints to the calf band.

13. The orthosis of claim 12 wherein said calf band includes a plurality of mounting holes longitudinally spaced apart on the calf band sides through which the fasteners selectively extend.

14. The orthosis of claim 1 wherein said upper splints have a plurality of longitudinally spaced apart mounting holes therethrough for selectively receiving fasteners which engage the upper splints and the thigh band, whereby the effective length of the upper splints is set by selection of the mounting holes through which the fasteners pass.

15. The orthosis of claim 1 wherein the lower ends of the lower splints are free from ambulatory structure.

16. The orthosis of claim 1 wherein the cover fits within the calf band.

17. A leg orthosis for an leg amputee having a residual limb, the orthosis comprising:

a pair of splints, each having upper and lower ends, and being positioned on opposite sides of the residual limb;

a curved calf band mounted to and extending between the splints for engaging the amputee'residual limb, and having opposite sides with a space therebetween for receiving the residual limb;

a cover removably mountable with the calf band after the residual limb is received in the calf band for closing the space therein and thereby defining an openable bivalve for enclosing the residual limb;

straps extending between the opposite sides of the calf band and over the cover for securing the band and cover around the residual limb; and padding on the band to engage the amputee'residual limb.

18. The orthosis of claim 17 wherein said cover is a curved member adapted to removably mate with and be overlapped by the calf band to close the space therein and enclose the residual limb.

19. The leg orthosis of claim 1 wherein the cover is a resilient single piece member.

20. The leg orthosis of claim 1 wherein the calf band and cover each have curvature extending more than 180° such that the calf band and cover have overlapping sides when the cover is mounted with the calf band.

* * * * *